United States Patent [19]

Krass et al.

[11] Patent Number: 5,410,042
[45] Date of Patent: Apr. 25, 1995

[54] PROCESS FOR THE CLEAVAGE OF CEPHALOSPORIN PRODRUG ESTERS TO 7-AMINO-3-METHOXYMETHYLCEPH-3-EM-4-CARBOXYLIC ACID

[75] Inventors: Norbert Krass, Frankfurt am Main; Elisabeth Defossa, Idstein/Taunus; Gerd Fischer, Limburg; Uwe Gerlach; Rolf Hoerlein, both of Frankfurt am Main; Rudolf Lattrell, Koenigstein/Taunus; Adolf H. Linkies, Frankfurt am Main; Wolfgang Martin, Kelkheim/Taunus; Ulrich Stache, Hofheim am Taunus; Theodor Wollmann, Hofheim am Taunus, all of Germany

[73] Assignee: Hoechst Aktiengesellschaft, Frankfurt am Main, Germany

[21] Appl. No.: 63,574

[22] Filed: May 19, 1993

[30] Foreign Application Priority Data

May 21, 1992 [DE] Germany .......... 42 16 881.3

[51] Int. Cl.$^6$ .......................... C07D 501/04
[52] U.S. Cl. ...................... 540/215; 540/228
[58] Field of Search .............. 540/215, 230, 228

[56] References Cited

U.S. PATENT DOCUMENTS

| | | | |
|---|---|---|---|
| 4,098,888 | 7/1978 | Ochiai et al. | 424/246 |
| 4,203,899 | 5/1980 | Ochiai et al. | 548/194 |
| 4,205,180 | 5/1980 | Ochiai et al. | 560/168 |
| 4,264,595 | 4/1981 | Numata et al. | 424/246 |
| 4,278,793 | 7/1981 | Dürckheimer et al. | 544/27 |
| 4,283,396 | 8/1981 | Heymes et al. | 424/246 |
| 4,298,606 | 11/1981 | Ochiai et al. | 424/246 |
| 4,355,160 | 10/1982 | Ochiai et al. | 544/27 |
| 4,409,215 | 10/1983 | Takaya et al. | 424/246 |
| 4,462,999 | 7/1984 | Takaya et al. | 424/246 |
| 4,483,855 | 11/1984 | Nakao et al. | 424/246 |
| 4,486,425 | 12/1984 | Nakao et al. | 424/246 |
| 4,514,565 | 4/1985 | Ochiai et al. | 540/25 |
| 4,668,783 | 5/1987 | Ochiai et al. | 540/222 |
| 4,904,652 | 2/1990 | Takaya et al. | 514/206 |
| 4,912,212 | 3/1990 | Ochiai et al. | 540/227 |
| 4,973,684 | 11/1990 | Ochiai et al. | 540/222 |
| 4,992,431 | 3/1991 | Heymes et al. | 514/202 |
| 5,026,695 | 6/1991 | Takaya et al. | 514/202 |
| 5,063,224 | 11/1991 | Mosher et al. | 514/202 |
| 5,100,887 | 3/1992 | Adam et al. | 514/195 |

FOREIGN PATENT DOCUMENTS

0034536B1  2/1981  European Pat. Off. .

(List continued on next page.)

OTHER PUBLICATIONS

Kamiya, T., et al., "Tentative Protection of Carboxyl Groups," Chem. Abstracts 82 (1975), p. 517, No. 112093g.

Kamiya, T., et al., "Carboxy Group–Containing Compounds," Chem. Abstracts 82 (1975), p. 501, No. 3138p.

Kametani, T., et al., "The Deblocking of Cephalosporin Benzhydryl Esters With Formic Acid," Chem. Abstracts 98 (1983), p. 625, No. 179032k.

Webber, J. A., et al., "Chemistry of Cephalosporin Antibiotics, XVII. Functionalization of Deacetoxycephalosporin. The Conversion of Penicillin into Cephalosporin," J. Am. Chem. Soc. 91 (20), p. 5974 (1969).

Ogliaruso, M. A., et al., Synthesis of Carboxylic Acids, Esters, and Their Derivatives; J. Wiley and Sons 1991, pp. 229–230.

Chandrasekaran, S., et al., "Synthesis of Substituted

*Primary Examiner*—Nicholas Rizzo
*Attorney, Agent, or Firm*—Finnegan, Henderson, Farabow, Garrett & Dunner

[57] ABSTRACT

The present invention relates to a process for the preparation of 7-amino-3-methoxymethylceph-3-em-4-carboxylic acid (I) from 7-amino-3-methoxymethylceph-3-em-4-carboxylic acid esters (II) or their salts by ester cleavage.

The process comprises treating the compound II with formic acid, trifluoroacetic acid, methanesulfonic acid or trifluoromethanesulfonic acid or a mixture of two of these acids in each case.

4 Claims, No Drawings

OTHER PUBLICATIONS

β-lactams by Addition of Nitromethane to 6-Oxopenicillanates and 7-Oxocephalosporanates," J. Org. Chem. 42 (24), 3972 (1977).
S. Torii et al., J. Org. Chem. 56:3633 (1991).
H. Kamachi et al., J. Antibiotics 41(11):1602 (1988).
K. Fujimoto et al., J. Antibiotics 40(3):370 (1987).
T. Nishimura et al., J. Antibiotics 40(1):81 (1987).
E. Defossa et al., Abstract No. 187, Cefdaloxime Pentexil Tosilate (HR916K): a Diastereomerically Pure Novel Oral Cephalosporinester: Synthesis and Antibacterial Activity In Vivo (Oct. 11–14, 1991).
D. Isert et al., Abstract No. 188, Cefdaloxime Pentexil Tosilate (HR916K): a Diastereomerically Pure Novel Oral Cephalosporinester with Outstanding Absorption Characteristics (Oct. 11–14, 1991).
"Cefpodoxime Proxetil", Drugs of the Future, 14(1):73–74 (1989).
"SCE-2174", Drugs of the Future, 13(3):231–233 (1988).
"Cefuroxime Axetil", Drugs of the Future, 10(2):112–113 (1985).
"Antibiotic Activity of CL 118,673, a New Oral Cephalosporin", N. A. Kuck et al., Recent Advances In Chemotherapy, Proceedings of the 14th Int'l. Congress of Chemotherpay, Antimicrobial Section 2, pp. 1137–1138 (1985).
Improved Synthesis of an Ester-Type Prodrug, 1-Acetoxyethyl 7-[(Z)-2-(2-Aminothiazol-4-yl)-2-Hydroxyiminoacetamido]-3-[(Z)-1-Propenyl]-3-Cephem-4-Carboxylate (BMY-28271), Hajime Kamachi et al., The Journal of Antibiotics, vol. XLIII(12):1564–1572 (1990).
"Beta-Lactam Compounds", Chemical Abstracts, 102:220658k (1985).
"Cephalosporin derivatives", Chemical Abstracts, 102:220657j (1985).

FOREIGN PATENT DOCUMENTS

| | | |
|---|---|---|
| 0034536A2 | 2/1981 | European Pat. Off. . |
| 0029557A2 | 6/1981 | European Pat. Off. . |
| 0034536A3 | 8/1981 | European Pat. Off. . |
| 0049118A2 | 4/1982 | European Pat. Off. . |
| 0049119A2 | 4/1982 | European Pat. Off. . |
| 0134420A1 | 3/1985 | European Pat. Off. . |
| 0156771A2 | 10/1985 | European Pat. Off. . |
| 0222022 | 5/1987 | European Pat. Off. . |
| 0329008A2 | 8/1989 | European Pat. Off. . |
| 0379132A2 | 7/1990 | European Pat. Off. . |
| 0531875A2 | 9/1990 | European Pat. Off. . |
| 0402806A1 | 12/1990 | European Pat. Off. . |
| 0514791A2 | 5/1992 | European Pat. Off. . |
| 2556736A1 | 6/1976 | Germany . |
| 2560398C2 | 9/1983 | Germany . |
| 3804841A1 | 8/1989 | Germany . |
| 3809561 | 10/1989 | Germany . |
| 3919259A1 | 12/1990 | Germany . |
| 60-004189A | 1/1985 | Japan . |
| 60-004190A | 1/1985 | Japan . |
| 2110688 | 6/1983 | United Kingdom . |

PROCESS FOR THE CLEAVAGE OF CEPHALOSPORIN PRODRUG ESTERS TO 7-AMINO-3-METHOXYMETHYLCEPH-3-EM-4-CARBOXYLIC ACID

The invention relates to a process for the preparation of 7-amino-3-methoxymethylceph-3-em-4-carboxylic acid (7-MACA) from 7-amino- 3-methoxymethylceph-3-em-4-carboxylic acid esters or their salts by ester cleavage.

The methods of ester cleavage known from the literature require reaction conditions which do not permit use for 7-amino-3-methoxymethylceph-3-em-4-carboxylic acid esters in a satisfactory manner because of the labile $\beta$-lactam ring. For example, the alkaline hydrolysis of esters with bases such as KOH, NaOH or sodium alkoxides in water or in organic solvents such as e.g. dioxane or alcohol leads only to decomposition products. The cleavage of cephalosporin esters by means of phenol and acid catalysis is described by S. Torii et al. (J. Org. Chem. 56 (1991) 3633). Use of this process for 7-amino-3-methoxy-methylceph-3-em-4-carboxylic acid esters, however, yielded the desired carboxylic acid only in low yield and inadequate purity.

For the synthesis of diastereomerically pure cephalosporin prodrug esters, as are described e.g. in EP-A-0 329 008, EP-A-0 514 791 and EP-A-0 531 875, it is essential that the 7-amino-3-methoxymethylceph-3-em-4-carboxylic acid esters, which after esterification of the corresponding carboxylic acids are obtained as a diastereomer mixture, are separated into the pure diastereomers. In this way, diastereomers having different pharmacological activity are obtained. The invention is therefore based on the object of developing a process with which 7-amino-3-methoxymethylceph-3-em-4-carboxylic acid esters, in particular, a less active diastereomer or even different mixtures thereof, can be converted into the corresponding carboxylic acids again in high yield and can thus be used for a fresh esterification.

This object is achieved according to the invention by the process for the preparation of 7-amino-3-methoxymethylceph-3-em-4-carboxylic acid of the formula I

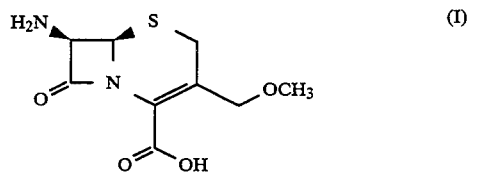

which comprises treating 7-amino-3-methoxymethylceph-3-em-4-carboxylic acid esters of the formula II or their salts

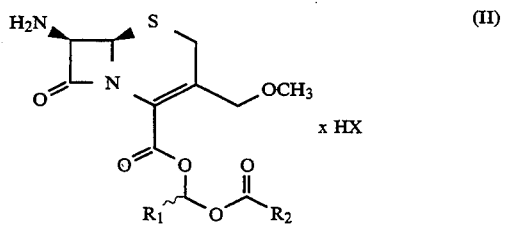

in which
$R^1$ is methyl or ethyl,
$R^2$ is $C_1$–$C_6$-alkyl or $C_1$–$C_6$-alkoxy and HX is a mono- or polybasic acid and X is an organic or inorganic anion, with an acid, preferably a mixture of two acids.

In $R^2$, $C_1$–$C_6$-alkyl can in this case be methyl, ethyl, n-propyl, isopropyl, n-butyl, isobutyl, tert-butyl, pentyl, cyclopentyl, hexyl or cyclohexyl, preferably n-propyl, isopropyl, n-butyl, tert-butyl or cyclohexyl, in particular tert-butyl; and $C_1$–$C_6$-alkoxy can be methoxy, ethoxy, n-propoxy, isopropoxy, n-butoxy, isobutoxy, tert-butoxy, n-pentyloxy, cyclopentyloxy, n-hexyloxy and cyclohexyloxy, preferably n-propoxy, isopropoxy, n-butoxy, tert-butoxy and cyclohexyloxy, particularly preferably isopropoxy.

The compounds of the formula II are employed as free bases or in the form of their salts (with HX), where HX is a mono- or polybasic acid and X can be an inorganic or organic, physiologically acceptable anion. As an inorganic acid, HX is, for example, stoichiometric amounts of HCl, HBr, HI, $HBF_4$, $HNO_3$, $HClO_4$, $H_2SO_4$ or $H_3PO_4$. As an organic acid, HX is aliphatic or aromatic sulfonic acids and formic acid, acetic acid or trifluoroacetic acid. HX is preferably the inorganic acids HCl, HBr and $H_2SO_4$ and the organic acids methanesulfonic acid, ethanesulfonic acid, benzenesulfonic acid, p-toluenesulfonic acid and 4-ethylbenzenesulfonic acid, formic acid, acetic acid and trifluoroacetic acid. The acids HCl, methanesulfonic acid and p-toluenesulfonic acid are particularly preferred.

The process according to the invention is distinguished in that compounds of the formula II are reacted with a protonic acid or a mixture of two acids. For this purpose, the following acids can be employed:
formic acid, trifluoroacetic acid, methanesulfonic acid and trifluoromethanesulfonic acid. Trifluoroacetic acid, methanesulfonic acid and trifluoromethanesulfonic acid and the following combinations are preferred:
trifluoroacetic acid/methanesulfonic acid, trifluoroacetic acid/trifluoromethanesulfonic acid, formic acid/sulfuric acid, formic acid/trifluoroacetic acid, formic acid/methanesulfonic acid and formic acid/trifluoromethanesulfonic acid. Formic acid/sulfuric acid, trifluoroacetic acid, methanesulfonic acid and trifluoromethanesulfonic acid or mixtures of two of these last-mentioned acids in each case are particularly preferred.

When using a mixture of two acids, the ratios of the molar equivalents are between 20:1 and 1:1, preferably between 12:1 and 5:1, in particular around a ratio of 10:1.

Relative to the cephalosporin ester employed, the amount of acid used can be between 1 and 20, preferably between and 12, in particular around 11 molar equivalents. If hexafluoroisopropanol is employed as a solvent, the amount of acid used can be between 1 and 2, preferably between 1 and 1.5 molar equivalents. If no particular solvent is used, the amount of cephalosporin ester:acid, however, is between 40 and 80, preferably between 50 and 60 molar equivalents.

The reaction of the process according to the invention can be carried out without solvent or alternatively with addition of one of the following solvents:
water, acetone, tetrahydrofuran, dioxane, diethyl ether, acetonitrile, dichloromethane, benzene, toluene, anisole and 1,1,1,3,3,3-hexafluoroisopropanol (HFIP). Dichloromethane, hexafluoroisopropanol, acetonitrile and toluene, in particular dichloromethane and hexafluoroisopropanol, are particularly preferred.

Depending on the solvent, the reaction temperature is between about −10° C. and +40° C., preferably between 0° C. and 25° C. (room temperature). The reaction is preferably carried out at room temperature if $CH_2Cl_2$ is used as a solvent and between 0° C. and +5° C. if HFIP is used as a solvent. Depending on the reaction temperature, solvent and acid addition product, the reaction time can be between 2 and 20 hours.

The 7-amino-methoxymethylceph-3-em-4-carboxylic acid (7-MACA) of the formula II prepared by the process according to the invention is worked up and isolated after hydrolysis with ice-water and precipitation by addition of base, such as e.g. ammonia, 10–40% strength potassium hydroxide solution or sodium hydroxide solution. The product is washed with water, acetone and diethyl ether and dried in a customary manner. Impurities can be removed by treating the product solution with active carbon or alternatively by stirring over or by chromatography on ®Diaion HP 20 (Mitsubishi Chem. Ind., Ltd.).

The process according to the invention is distinguished compared to other ester hydrolysis methods known from the literature in that it yields the compound of the formula I in good yield and very high purity. The product thus obtained is converted into mixtures of the general formula II by esterification analogously to the description in EP-A-0 329 008, EP-A-0 514 791 and EP-A-0 531 875, the compound of the formula I recyclized by the process according to the invention being characterized by the same reaction behavior as the commercially available 7-MACA from Biochemie (Kundl, Austria).

EXAMPLE 1

80 g (195.6 mmol) of 1-(2,2-dimethylpropionyloxy)ethyl 7-amino-3-methoxymethylceph-3-em-4-carboxylate hydrochloride are suspended in 400 ml of methylene chloride and treated with 222.4 g (1.95 mol) of trifluoroacetic acid and 18.8 g (195.6 mmol) of methanesulfonic acid. After stirring at room temperature for 2 hours, the reaction mixture is concentrated in vacuo and the oily residue is taken up in 120 ml of water. The solution is stirred for 10 minutes over 160 g of ®Diaion HP 20 (Mitsubishi Chem. Ind., Ltd.), and the solid is filtered off with suction through a suction filter and washed with 400 ml of water. The filtrate is treated with 10 g of ®Clarocarbon F (Merck 2508), and the active carbon is removed by means of filter layers and washed with 40 ml of water. The product is precipitated by addition of conc. $NH_4OH$ with ice-cooling at a pH of 2.5. The solid is filtered off, washed twice with 100 ml each of water, acetone and ether and dried in an oil pump vacuum.

Yield: 27 g (57%) of 7-amino-3-methoxymethyl-ceph-3-em-4-carboxylic acid (7-MACA). $^1$H NMR (270 MHz, DMSO-$d_6$): δ=3.20 (s,3H,$OCH_3$); 3.35–3.60 (AB System,2H,$SCH_2$); 4.15 (s,2H,$OCH_2$); 4.76 (d,1H,H-6); 4.98 (d,1H,C-7).

EXAMPLE 2

5.0 g (9.2 mmol) of the p-toluenesulfonate of 1-(2,2-dimethylpropionyloxy)ethyl 7-amino-3-methoxymethylceph-3-em-4-carboxylate in 20 ml of methylene chloride are treated with 10.46 g (91.7 mmol) of trifluoroacetic acid and the mixture is stirred at room temperature for 16 hours. After concentration of the reaction mixture in vacuo, the residue is taken up in water, filtered through active carbon and chromatographed on 10 g of ®Diaion HP 20 (Mitsubishi Chem. Ind., Ltd.) using 2N hydrochloric acid as the eluent. The combined product fractions are concentrated in vacuo to half the original volume and the pH of the solution is adjusted to a value of 2.5 by addition of conc. $NH_4OH$ with ice-cooling. After 30 minutes at 0° C. the precipitated 7-MACA is filtered off with suction and washed successively with water, acetone and diethyl ether.

Yield: 1.4 g (62%) of white solid, identical to the product from Example 1.

EXAMPLE 3

A solution of 4.91 g (9.0 mmol) of 1-(2,2-dimethylpropionyloxy)ethyl 7-amino-3-methoxymethylceph-3-em-4-carboxylate toluenesulfonate are suspended in 20 ml of formic acid and treated with 0.2 ml of conc. sulfuric acid. After stirring at room temperature for 3 hours, the reaction solution is filtered through ®Diaion HP 20 and eluted with 2N HCl. Subsequent isolation of the 7-MACA is carried out analogously to Example 2.

Yield: 590 mg (27%).

EXAMPLE 4

4.3 g (10.5 mmol) of 1-(2,2-dimethylpropionyloxy)ethyl 7-amino-3-methoxymethylceph-3-em-4-carboxylate hydrochloride are dissolved in 50 ml of hexafluoroisopropanol and treated with 0.8 ml (12.3 mmol) of methanesulfonic acid. After 17 hours at 0°–5° C., 20 g of ice are added to the reaction mixture and the pH is adjusted to a value of 2.5 using conc. $NH_4OH$. Hexafluoroisopropanol is removed by distillation in vacuo at room temperature, the pH is readjusted to 2.5 and the aqueous suspension is stirred at 0° C. for a further 60 minutes to complete precipitation. The solid is filtered off with suction and washed with ice-water, methanol and acetone. The crude product is dissolved in a hydrochloric acid/ice-water mixture and purified by addition of active carbon ( ®Clarocarbon F, Merck 2508). After filtration, the 7-amino-3-methoxymethylceph-3-em-4-carboxylic acid can be reprecipitated as described above.

Yield: 1.9 g (74%) of white solid.

EXAMPLE 5

10 g (24.4 mmol) of 1-(2,2-dimethylpropionyloxy)ethyl 7-amino-3-methoxymethylceph-3-em-4-carboxylate hydrochloride are suspended in a solution of 5 g of sodium bicarbonate in 60 ml of water, treated with 100 ml of ethyl acetate and stirred at room temperature for 20 minutes. The phases are separated and the aqueous phase is extracted twice with 50 ml of ethyl acetate each time. The combined organic phases are concentrated in vacuo and the residue is treated with 4.66 g (24.5 mmol) of p-toluenesulfonic acid hydrate. After 1 minute, 100 ml of trifluoroacetic acid are added to the reaction mixture and it is stirred at room temperature for 3 hours. Further carrying-out takes place as described in Example 4.

Yield: 4.08 g (70%) of colorless crystals.

COMPARISON EXAMPLE

Analogously to Torii et al. (J. Org. Chem. 56 (1991) 3633), a suspension of 1.09 g (2.0 mmol) of 1-(2,2-dimethylpropionyloxy)ethyl 7-amino-3-methoxymethylceph-3-em-4-carboxylate tosylate in 4 ml of acetonitrile is treated with 0.94 g (10 mmol) of phenol and 1.154 ml (2.0 mmol) of trifluoroacetic acid and the mixture is stirred at 40° C. The reaction is checked by HPLC (®LiChrosorb RP18, 250×4 mm; Hibar) eluent: A=MeOH/water 4:1+0.1% NH4OAc, gradient with water (eluent B) until A/B=6:4). After 6 hours, the starting material has completely reacted, a complex product mixture being formed. Reference measurements by means of HPLC confirm that the desired 7-MACA is contained in the mixture only in a relative proportion of 3.5%.

We claim:

1. A process for the preparation of a compound of the formula I

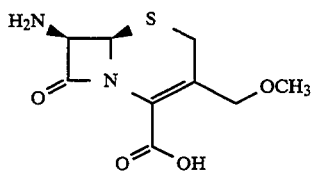

that comprises treating an ester of the formula II or a salt thereof of the formula II

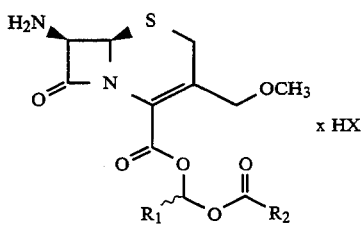

wherein:
- $R^1$ is methyl or ethyl;
- $R^2$ is $C_1$-$C_6$-alkyl or $C_1$-$C_6$-alkoxy; and
- HX is an acid selected from the group consisting of HCl, HBr, $H_2SO_4$, methanesulfonic acid, ethanesulfonic acid, benzenesulfonic acid, 4-ethylbenzenesulfonic acid, P-touluenesulfonic acid, formic acid, acetic acid, and trifluoroacetic acid;

with an acid selected from the group consisting of trifluoroacetic acid, methanesulfonic acid, trifluoromethanesulfonic acid, and a mixture of any two of these acids, the molar ratio of acid and ester of formula II being between 1:1 and 20:1 in case a solvent is used, and between 40:1 and 80:1 in case of the absence of a solvent, and at a temperature of from 0° to 25° C.

2. The process for the preparation of 7-amino-3-methoxymethylceph-3-em-4-carboxylic acid of the formula I as claimed in claim 1, wherein the compounds of the formula II are reacted with a protonic acid or a mixture of two acids, such as formic acid, trifluoroacetic acid, methanesulfonic acid and trifluoromethanesulfonic acid.

3. The process for the preparation of 7-amino-3-methoxymethylceph-3-em-4-carboxylic acid of the formula I as claimed in claim 2, wherein trifluoroacetic acid, methanesulfonic acid and trifluoromethanesulfonic acid and combinations such as trifluoroacetic acid/methanesulfonic acid, trifluoroacetic acid/trifluoromethanesulfonic acid, formic acid/sulfuric acid, formic acid/trifluoroacetic acid, formic acid/methanesulfonic acid and formic acid/trifluoromethanesulfonic acid are used.

4. The process as defined in claim 1, wherein the molar ratio of acid and ester is between 8:1 and 12:1, and the solvent is dichloromethane or hexfluoroisopropanol.

* * * * *